(12) United States Patent  
Grüne et al.

(10) Patent No.: US 9,963,408 B2  
(45) Date of Patent: May 8, 2018

(54) PROCESS FOR PREPARING 1,3-BUTADIENE FROM N-BUTENES BY OXIDATIVE DEHYDROGENATION

(71) Applicant: BASF SE, Ludwigshafen (DE)

(72) Inventors: Philipp Grüne, Mannheim (DE); Oliver Hammen, Wintersheim (DE); Christine Schmitt, Mannheim (DE); Ragavendra Prasad Balegedde Ramachandran, Limburgerhof (DE); Jan Pablo Josch, Neustadt (DE); Christian Walsdorff, Ludwigshafen (DE)

(73) Assignee: BASF SE (DE)

( * ) Notice: Subject to any disclaimer, the term of this patent is extended or adjusted under 35 U.S.C. 154(b) by 186 days.

(21) Appl. No.: 15/033,203

(22) PCT Filed: Oct. 27, 2014

(86) PCT No.: PCT/EP2014/072978  
§ 371 (c)(1),  
(2) Date: Apr. 29, 2016

(87) PCT Pub. No.: WO2015/063019  
PCT Pub. Date: May 7, 2015

(65) Prior Publication Data  
US 2016/0355450 A1    Dec. 8, 2016

(30) Foreign Application Priority Data  
Oct. 30, 2013    (EP) ..................... 13190897

(51) Int. Cl.  
*C07C 5/48*    (2006.01)  
*B01J 23/00*    (2006.01)  
(Continued)

(52) U.S. Cl.  
CPC ............ *C07C 5/48* (2013.01); *B01J 23/002* (2013.01); *B01J 23/8878* (2013.01);  
(Continued)

(58) Field of Classification Search  
CPC .... C07C 5/48; C07C 7/08; C07C 7/11; C07C 11/167; C07C 2523/04; C07C 2523/18;  
(Continued)

(56) References Cited

U.S. PATENT DOCUMENTS 3,890,123 A    6/1975   Kuga  
3,911,039 A    10/1975   Grasselli et al.  
(Continued)

FOREIGN PATENT DOCUMENTS

DE    2440329 A1    3/1975  
DE    2447825 A1    8/1975  
(Continued)

OTHER PUBLICATIONS

Database WPI Week 198531 Thomson Scientific, London, GB; AN 1985-187149 XP002724652, & JPS60115532A (Nippon Zeon Co. Ltd.) Jun. 22, 1985 (Jun. 22, 1985).  
(Continued)

*Primary Examiner* — Brian A McCaig  
*Assistant Examiner* — Jason Y Chong  
(74) *Attorney, Agent, or Firm* — Drinker Biddle & Reath LLP

(57) ABSTRACT

A process for preparing butadiene from n-butenes, comprising the steps of:
     absorbing C4 hydrocarbons comprising butadiene and n-butenes, obtained from oxidative dehydrogenation of n-butenes, in an aromatic hydrocarbon solvent as an absorbent and removing uncondensable and low-boiling gas constituents comprising oxygen, low-boiling hydrocarbons, any carbon oxides, aromatic hydrocar-  
(Continued)

bon solvent and any inert gases as gas stream d2, giving an absorbent stream laden with C4 hydrocarbons and the gas stream d2, and then desorbing the C4 hydrocarbons from the laden absorbent stream, giving a C4 product gas stream d1;

and at least partly recycling the gas stream d2 as cycle gas stream a2 into the oxidative dehydrogenation zone, wherein the content of aromatic hydrocarbon solvent in the cycle gas stream a2 is limited to less than 1% by volume.

6 Claims, 1 Drawing Sheet

(51) Int. Cl.
  *B01J 23/887* (2006.01)
  *C07C 7/08* (2006.01)
  *C07C 7/11* (2006.01)
  *B01J 37/00* (2006.01)

(52) U.S. Cl.
  CPC ............ *B01J 37/0045* (2013.01); *C07C 7/08* (2013.01); *C07C 7/11* (2013.01); *B01J 2523/00* (2013.01); *C07C 2523/04* (2013.01); *C07C 2523/18* (2013.01); *C07C 2523/26* (2013.01); *C07C 2523/28* (2013.01); *C07C 2523/745* (2013.01); *C07C 2523/75* (2013.01); *C07C 2523/887* (2013.01)

(58) Field of Classification Search
  CPC ............ C07C 2523/26; C07C 2523/28; C07C 2523/745; C07C 2523/75; C07C 2523/887; B01J 23/002; B01J 23/8878; B01J 37/0045; B01J 2523/00
  See application file for complete search history.

(56) References Cited

U.S. PATENT DOCUMENTS

| | | |
|---|---|---|
| 3,932,551 A | 1/1976 | Grasselli et al. |
| 3,956,181 A | 5/1976 | Grasselli et al. |
| 4,141,706 A | 2/1979 | Regehr |
| 4,162,234 A | 7/1979 | Grasselli et al. |
| 4,336,409 A | 6/1982 | Yamamoto et al. |
| 4,397,771 A | 8/1983 | Grasselli et al. |
| 4,423,281 A | 12/1983 | Yamamoto et al. |
| 4,424,141 A | 1/1984 | Grasselli et al. |
| 4,547,615 A | 10/1985 | Yamamoto |
| 2008/0183024 A1* | 7/2008 | Klanner ............... C07C 5/3337 585/633 |
| 2012/0130137 A1 | 5/2012 | Orita et al. |
| 2015/0126788 A1* | 5/2015 | Takagaki ............... C07C 7/10 585/326 |

FOREIGN PATENT DOCUMENTS

| | | | |
|---|---|---|---|
| DE | 2530959 A1 | 2/1976 | |
| DE | 26 00 128 A1 | 7/1976 | |
| JP | S60115532 A | 6/1985 | |
| JP | 2010090083 A | 4/2010 | |
| JP | 2011001341 A | 1/2011 | |
| JP | 2011006381 A | 1/2011 | |
| JP | 2012072086 A | 4/2012 | |
| KR | 20130036467 A | 4/2013 | |
| KR | 20130036468 A | 4/2013 | |
| WO | WO-2013136434 A1 * | 9/2013 | ............ C07C 7/10 |

OTHER PUBLICATIONS

Database WPI Week 201107 Thomson Scientific, London, GB; AN 2011-A58751 XP002724651, & JP20100089647 (Nippon Signal Co. Ltd.) Apr. 8, 2010 (Apr. 8, 2010).

Database WPI Week 201230 Thomson Scientific, London, GB; AN 2012-E48215 XP002724650, & JP2012072086 (Asahi Kesei KK) Apr. 12, 2012 (Apr. 12, 2012).

International Preliminary Examination Report (in German) for PCT/EP2014/072978 dated Nov. 4, 2015.

International Search Report for PCT/EP2014/072978 dated Jan. 23, 2015.

* cited by examiner

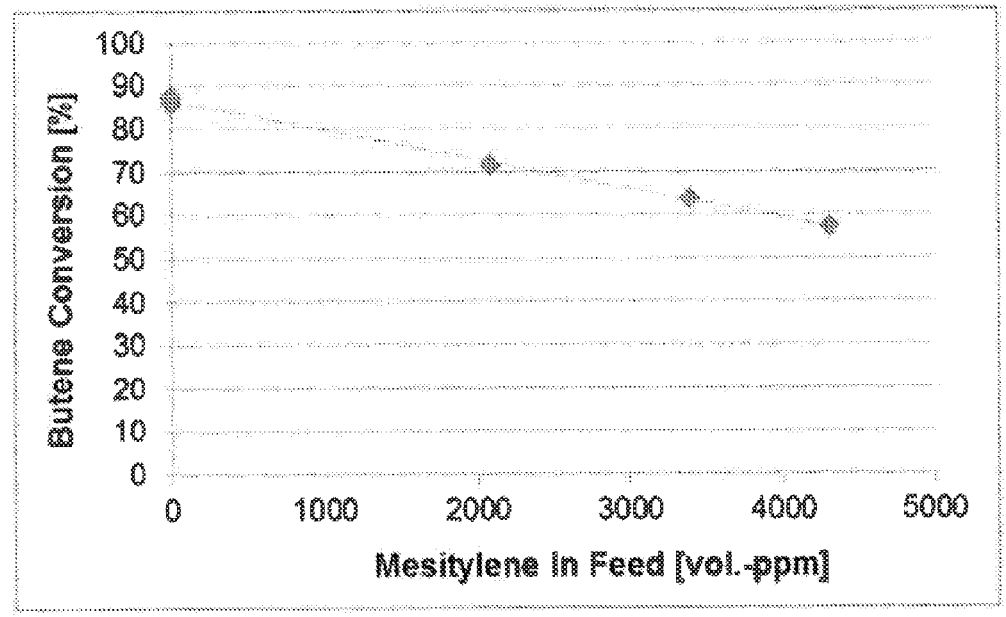

PROCESS FOR PREPARING 1,3-BUTADIENE FROM N-BUTENES BY OXIDATIVE DEHYDROGENATION

CROSS-REFERENCE TO RELATED APPLICATIONS

This application is a national stage application (under 35 U.S.C. § 371) of PCT/EP2014/072978, filed Oct. 27, 2014, which claims benefit of European Application No. 13190897.2, filed Oct. 30, 2013, both of which are incorporated herein by reference in their entirety.

FIELD OF THE INVENTION

The invention relates to a process for preparing 1,3-butadiene from n-butenes by oxidative dehydrogenation (ODH).

BACKGROUND OF THE INVENTION

Butadiene (1,3-butadiene) is an important base chemical and is used, for example, for production of synthetic rubbers (butadiene homopolymers, styrene-butadiene rubber or nitrile rubber) or for production of thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Through dimerization of butadiene, it is also possible to obtain vinylcyclohexene, which can be dehydrogenated to styrene.

Butadiene can be prepared by thermal cracking (steamcracking) of saturated hydrocarbons, typically proceeding from naphtha as the raw material. The steamcracking of naphtha affords a hydrocarbon mixture of methane, ethane, ethene, acetylene, propane, propene, propyne, allene, butanes, butenes, butadiene, butynes, methylallene, and $C_5$ and higher hydrocarbons.

Butadiene can also be obtained by the oxidative dehydrogenation of n-butenes (1-butene and/or 2-butene) in the presence of molecular oxygen. The input gas stream utilized for the oxidative dehydrogenation (oxydehydrogenation, ODH) of n-butenes to butadiene may be any desired mixture comprising n-butenes. For example, it is possible to use a fraction which comprises n-butenes (1-butene and/or 2-butene) as the main constituent and has been obtained from the $C_4$ fraction from a naphtha cracker by removing butadiene and isobutene. In addition, it is also possible to use gas mixtures which comprise 1-butene, cis-2-butene, trans-2-butene or mixtures thereof and have been obtained by dimerization of ethylene as the input gas stream. In addition, the input gas streams used may be gas mixtures which comprise n-butenes and have been obtained by catalytic fluidized bed cracking (fluid catalytic cracking, FCC).

As well as n-butenes and molecular oxygen, the reaction gas mixture generally comprises inert components. "Inert components" means here that they are converted to an extent of less than 90% under the reaction conditions of the ODH. Inert components are, for example, steam and nitrogen, but also, for example, alkanes such as methane. The molar ratio of the inert component to molecular oxygen here is generally higher than is present in air, particularly in order to avoid the risk of explosions. This can be done, for example, by using air as the oxygenous gas and diluting it with molecular nitrogen. However, the provision of large volumes of concentrated nitrogen is costly and disadvantageous from an economic point of view. In addition, this can be done by using molecular oxygen-depleted air (lean air) as the oxygenous gas. In addition, this can be done by diluting air with lean air.

Processes for oxidative dehydrogenation of butenes to butadiene are known in principle.

US 2012/0130137A1, for example, describes a process of this kind using catalysts comprising oxides of molybdenum, bismuth and generally further metals. For the lasting activity of such catalysts for the oxidative dehydrogenation, a critical minimum level of partial oxygen pressure is required in the gas atmosphere in order to avoid an excessive reduction and hence loss of performance of the catalysts. For this reason, it is generally also not possible to work with a stoichiometric oxygen input or complete oxygen conversion in the oxydehydrogenation reactor (ODH reactor). US 2012/0130137 describes, for example, an oxygen content of 2.5 to 8% by volume in the starting gas.

The $N_2/O_2$ ratio in the reaction gas mixture is set to the desired value by diluting air as the oxygenous gas with nitrogen gas.

The need for an oxygen excess for such catalyst systems is common knowledge and is reflected in the process conditions when catalysts of this kind are used. Representative examples include the comparatively recent studies by Jung at al. (Catal. Surv. Asia 2009, 13, 78-93; DOI 10.1007/s10563-009-9069-5 and Applied Catalysis A: General 2007, 317, 244-249; DOI 10.1016/j.apcata.2006.10.021).

The presence of oxygen alongside butadiene downstream of the ODH reactor stage, in the workup section of such processes operated with an excess of oxygen, however, is afflicted with risks. Especially in the liquid phase, the formation and accumulation of organic peroxides should be examined. These risks have been discussed, for example, by D. S. Alexander (Industrial and Engineering Chemistry 1959, 51, 733-738).

JP 2011-006381 A to Mitsubishi addresses the risk of peroxide formation in the workup section of a process for preparing conjugated alkadienes. As a solution, the addition of polymerization inhibitors to the absorption solutions for the process gases and the setting of a maximum peroxide content of 100 ppm by weight by heating the absorption solutions is described. However, there is no information as to avoidance or monitoring of peroxides in upstream process steps. A particularly critical aspect is the step of cooling the ODH reactor output with a water quench. Organic peroxides formed are barely soluble in water, and so they are deposited and can accumulate in the apparatus in solid or liquid form, instead of being discharged with the aqueous purge stream from the quench. At the same time, the temperature of the water quench is not so high that sufficiently high and constant breakdown of the peroxides formed can be assumed The catalytic oxidative dehydrogenation can form highboiling secondary components, for example maleic anhydride, phthalic anhydride, benzaldehyde, benzoic acid, ethylbenzene, styrene, fluorenone, anthraquinone and others. Such deposits can lead to blockages and to a rise in the pressure drop in the reactor or beyond the reactor in the workup area, and thus disrupt regulated operation. Deposits of the high-boiling secondary components mentioned can also impair the function of heat exchangers or damage moving apparatuses such as compressors. Steam-volatile compounds such as fluorenone can get through a quench apparatus operated with water and precipitate beyond it in the gas discharge lines. In principle, there is therefore also the risk that solid deposits will get into downstream apparatus parts, for example compressors, and cause damage there.

US 2012/0130137A1 paragraph [0122] also refers to the problem of high-boiling by-products. Particular mention is made of phthalic anhydride, anthraquinone and fluorenone, which are said to be present typically in concentrations of 0.001 to 0.10% by volume in the product gas. US 2012/0130137A1 paragraphs [0124]-[0126] recommends cooling the hot reactor discharge gases directly, by contact with a cooling liquid (quench tower), at first to typically 5 to 100° C. The cooling liquids mentioned are water or aqueous alkali solutions. There is explicit mention of the problem of blockages in the quench by high boilers from the product gas or by polymerization products of high-boiling, by-products from the product gas, and for this reason it is said to be advantageous that high-boiling by-products are entrained as little as possible from the reaction section to the cooling section (quench).

KR 2013-0036467 and KR 2013-0038468 likewise recommend cooling the hot reactor discharge gases directly by contact with a coolant. The coolants used are water-soluble organic coolants, in order to better cool the secondary component.

JP 2011-001341A describes a two-stage cooling operation for a process for oxidative dehydrogenation of alkenes to conjugated alkadienes. This involves first setting the product discharge gas from the oxidative dehydrogenation to a temperature between 300 and 221° C. and then cooling it further to a temperature between 99 and 21° C. Paragraphs [0066] ff. state that the temperature between 300 and 221° C. is preferably established using heat exchangers, but a portion of the high boilers could also precipitate out of the product gas in these heat exchangers. JP 2011-001341A therefore describes occasional washing of deposits out of the heat exchangers with organic or aqueous solvents. Solvents described are, for example, aromatic hydrocarbons such as toluene or xylene, or an alkaline aqueous solvent, for example the aqueous solution of sodium hydroxide. In order to avoid excessive frequency of shutdown of the process to clean the heat exchanger, JP2011-001341A describes a setup having two heat exchangers arranged in parallel, which are each alternately operated or washed (called A/B operation mode).

JP 2010-90083 A describes a process for oxidative dehydrogenation of n-butenes to butadiene, in which the product gas of the oxidative dehydrogenation is cooled and dewatered. Subsequently, butadiene and unconverted butenes and butane are absorbed in a solvent from the C4-containing input gas stream. The residual gas which has not been absorbed by the solvent is subsequently disposed of by incineration. If a solvent such as toluene having a low boiling point is used as the absorbent, this is recovered from the residual gas stream by absorption in a solvent having a high boiling point for example decane, for the purpose of avoidance of solvent losses.

JP 2012072086 states, in paragraph [0014], that a gas in which the hydrocarbons, such as butadiene, n-butene, n-butane, isobutane, have been removed from the product gas mixture can be recycled into the oxydehydrogenation as an oxygenous gas. The document does not make any statements about how such a recycle gas stream is obtained, and which impurities are present therein.

BRIEF SUMMARY OF THE INVENTION

It is an object of the present invention to provide a process which remedies the abovementioned disadvantages of known processes. More particularly, a process in which deposits resulting from high-boiling organic secondary constituents in the apparatuses connected downstream of the ODH are avoided is to be provided. In addition, a process in which the possible accumulation of organic peroxides is avoided is to be provided. It is a further object of the invention to reduce high levels of contamination of wastewater with organic compounds in dissolved, emulsified or suspended form, and the occurrence of wastewater contaminated with organic compounds. These objects are to be achieved without impairment of the catalyst activity by traces of organic solvents in the cycle gas recycled into the ODH.

The object is achieved by a process for preparing butadiene from n-butenes, comprising the steps of:
A) providing an input gas stream a1 comprising n-butenes,
B) feeding the input gas stream a1 comprising n-butenes, an oxygenous gas and an oxygenous cycle gas stream a2 into at least one oxidative dehydrogenation zone and oxidatively dehydrogenating n-butenes to butadiene, giving a product gas stream b comprising butadiene, unconverted n-butenes, steam, oxygen, low-boiling hydrocarbons and high-boiling secondary components, with or without carbon oxides and with or without inert gases,
Ca) cooling the product gas stream b and optionally at least partly removing high-boiling secondary components and steam, giving a product gas stream b',
Cb) compressing and cooling the product gas stream b' in at least one compression and cooling stage, giving at least one aqueous condensate stream c1 and one gas stream c2 comprising butadiene, n-butenes, steam, oxygen and low boiling hydrocarbons, with or without carbon oxides and with or without inert gases,
Da) absorbing the $C_4$ hydrocarbons comprising butadiene and n-butenes in an aromatic hydrocarbon solvent as an absorbent and removing uncondensable and low-boiling gas constituents comprising oxygen, low-boiling hydrocarbons, any carbon oxides, aromatic hydrocarbon solvent and any inert gases as gas stream d2 from the gas stream c2, giving an absorbent stream laden with $C_4$ hydrocarbons and the gas stream d2, and then desorbing the $C_4$ hydrocarbons from the laden absorbent stream, giving a $C_4$ product gas stream d1,
Db) at least partly recycling the gas stream d2 as cycle gas stream a2 into the oxidative dehydrogenation zone,
wherein the content of aromatic hydrocarbon solvent in the cycle gas stream a2 is limited to less than 1% by volume.

A BRIEF DESCRIPTION OF THE FIGURE

The FIGURE shows the Butene conversion based on the mesitylene in feed (volume-ppm) as shown in Table 2.

The proportion by volume of mesitylene and the further gas constituents is determined by gas chromatography. Calibration for mesitylene is effected here by means of an external standard. For this purpose, a gasifiable solvent, for example m-xylene, is dissolved together with mesitylene in a particular molar ratio in a solvent, for example acetone. Under the assumption that the two substances and the solvent behave as ideal gases, the mole fraction is converted to parts by volume.

The gas sample with a known proportion by volume of the gasifiable solvent is supplied to the GC via a sample loop. The sample loop of defined volume is operated at constant pressure and constant temperature, and it is then possible to determine an external factor from the areas for the comparative substance and for mesitylene. This factor can now be expressed in relation to mesitylene.

The further components are calibrated individually or in mixtures in a similar manner. In doing this, all components are treated like ideal gases. This applies equally to the analysis of the gas streams in the ODH process.

It has been found that elevated amounts of aromatic hydrocarbon solvents in the reaction mixture for the oxydehydrogenation impair the catalyst activity. The amount of aromatic hydrocarbon solvent in the reaction gas mixture depends particularly on the proportion of the aromatic hydrocarbon solvent in the cycle gas, and particularly on the proportion of the cycle gas in the reaction gas mixture.

The choice of coolant in the cooling stage Ca) is not subject to any restrictions. However, preference is given to using an organic solvent in the cooling stage Ca). These organic solvents generally have a very much higher dissolution capacity for the high-boiling by-products which can lead to deposits and blockages in the plant parts downstream of the ODH reactor than water or aqueous alkaline solutions. Preferred organic solvents used as coolants are aromatic hydrocarbons, more preferably toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is given to aromatic hydrocarbons having a boiling point at 1013.25 hPa of more than 120° C., or mixtures thereof. Mesitylene is especially preferred.

The absorbent used in the removal stage Da) is an aromatic hydrocarbon solvent. Preference is given to toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is given to aromatic hydrocarbons having a boiling point at 1013.25 hPa of more than 120° C. Particular preference is given to mesitylene. More particularly, in the removal stage Da), the same aromatic hydrocarbon solvent is used as in the preceding cooling stage Ca), when an organic solvent is used in the cooling stage Ca).

Absorption of the $C_4$ hydrocarbons comprising butadiene and n-butenes from the gas stream c2 in the aromatic hydrocarbon solvent gives uncondensable and low-boiling gas constituents comprising oxygen, low-boiling hydrocarbons, any carbon oxides and any inert gases as gas stream d2. At least a portion of this gas stream d2 is recycled as cycle gas stream a2 into the oxidative dehydrogenation (step B)). According to the invention, the content of aromatic hydrocarbon solvent in the cycle gas stream a2 is less than 1% by volume.

In one embodiment of the invention, the content of aromatic hydrocarbon solvent in the cycle gas stream a2 is limited to less than 1% by volume by operating the removal stage Da) at temperatures preferably below 50° C., more preferably at below 40° C., and/or at a pressure higher than 5 bar absolute, more preferably at 10 bar absolute or higher. To set the temperature, it is possible, for example, to cool the absorbent used in the removal stage Da) to a low temperature prior to entry into the removal stage Da).

In a further embodiment of the invention, the content of aromatic hydrocarbon solvent in the cycle gas stream a2 is limited to less than 1% by volume by contacting the gas stream which leaves the removal stage Da) with a liquid absorbent for the aromatic hydrocarbon solvent in a further column. The absorbent used in this further column has to be miscible with the aromatic hydrocarbon solvent from the absorber column of the removal stage Da), and may optionally also be the same solvent. If the absorbent used in the further column is the same solvent, the pressure in this further column is higher than in the absorber column of the removal stage Da), or else the absorbent stream fed to this further column is colder than the gas stream which enters this column, as a result of which the aromatic hydrocarbon solvent present in the gas stream d2 is at least partly removed.

In a further embodiment of the invention, the content of aromatic hydrocarbon solvent in the cycle gas stream a2 is limited to less than 1% by volume by contacting the gas stream d2 which leaves the removal stage Da) with a solid adsorbent which adsorbs the aromatic hydrocarbon solvent. In this case, it is possible to use adsorbents, for example activated carbon, through which the stream d2 is passed. Suitable adsorbents are described, for example, in Ullmann's Encyclopedia of Industrial Chemistry (2011), 7, 209-210 and 3, 527-528.

In a further embodiment of the invention, the content of aromatic hydrocarbon solvent in the cycle gas stream a2 is limited to less than 1% by volume by contacting the gas stream d2 which leaves the removal stage Da) with a heat exchanger in the form of a condenser, with at least partial deposition of the aromatic hydrocarbon solvent present in stream d2 as a liquid phase through cooling.

In a further embodiment of the invention, the content of aromatic hydrocarbon solvent in the cycle gas stream a2 is limited to less than 1% by volume by a thermal or catalytic post combustion of the aromatic hydrocarbon solvent. Suitable catalysts for a catalytic post combustion have been described many times in the literature; see, for example, Prasad et al., Catel. Rev. Sci. Eng. 26 (1984), 1; Trimm, Appl. Catal. 7 (1983), 249; Arai et al., Catal. Today 26 (1995), 217; Centi, J. Mol. Catal. 173 (2001), 287; Kirchnerova, Kor. J. Chem. Eng. 16 (1999), 427; Ciuparu et al., Catal. Rev. Sci. Eng. 44 (2002), 593 and literature cited therein.

The combustion oxidizes at least portions of the combustible constituents of the cycle gas in the presence of oxygen. Combustible constituents of the cycle gas are, for example, CO and the aromatic hydrocarbon solvent. In order to increase the combustibility of the cycle gas, it may be advantageous to add further combustible constituents to the cycle gas, for example methane, ethane or hydrogen.

The combustion can be effected adiabatically, auto thermally or isothermally, for example in a fluidized bed, in a staged oven, in a fixed bed tubular reactor or shell and tube reactor, or in a plate heat exchanger reactor. The flow through the bed can be aligned either axially or radially. Monolith reactors can be used for reactions which require little catalyst, advantageously in the form of an adiabatic reactor.

The entrance temperature for the cycle gas in the catalyst bed is typically more than 100° C., preferably more than 200° C. In order to reach these temperatures, the cycle gas can be preheated.

In a further embodiment of the invention, the content of aromatic hydrocarbon solvent in the cycle gas stream a2 is limited to less than 1% by volume by providing, in or downstream of the absorption column used in the absorption step Da), one or more apparatuses, for example a demister or droplet separator, which reduce the entrainment of liquid constituents from the absorption column into the gas stream d2. Suitable apparatuses are all of those which reduce the proportion of liquid constituents in the gas stream d2. In general, demisters or droplet separators are understood to mean apparatuses for separation of ultrafine liquid droplets out of gases, vapors or mists, generally aerosols. In columns, it is possible to reduce liquid entrainment by means of demisters or droplet separators. Demisters or droplet separators may consist, for example, of wire knit packings, lamellar separators or beds of random packings having high internal surface area. In general, the materials used are steels, chromium-nickel steels, aluminum, copper, nickel, polypropylene, polytetrafluoroethylene and the like. The separation level decreases with decreasing droplet diameters. Demisters can be counted among the coalescence separators. Demisters are described, inter alia, in applications U.S. Pat. No. 3,890,123 and U.S. Pat. No. 4,141,706 and the documents cited therein. The demister or droplet separator may either be within the absorption column or absorption columns, or be connected downstream thereof.

Preferably, the content of aromatic hydrocarbon solvent in the cycle gas stream a2 is less than 0.5% by volume, more preferably less than 0.2% by volume, especially less than 0.1% by volume.

Preferably, the process according the invention also comprises the following further process steps:

E) separating the $C_4$ product stream d1 by extractive distillation with a butadiene-selective solvent into a stream e1 comprising butadiene and the selective solvent and a stream e2 comprising n-butenes;

F) distilling the stream e2 comprising butadiene and the selective solvent to give a stream f1 comprising the selective solvent and a stream f2 comprising butadiene.

Embodiments which follow are preferred or particularly preferred variants of the process according to the invention:

Stage Ca) may be preceded upstream by at least one cooling stage in which the product gas stream b is cooled by indirect cooling in a heat exchanger.

Stage Ca) can be performed in multiple stages in stages Ca1) to Can), preferably in two stages. Ca1) and Ca2). In this case, particular preference is given to feeding at least a portion of coolant as coolant to the first stage Ca1) after it has passed through the second stage Ca2).

Stage Cb) generally comprises at least one compression stage Cba) and at least one cooling stage Cbb). Preferably, in the at least one cooling stage Cbb), the gas compressed in the compression stage Cba) is contacted with a coolant. More preferably, the coolant for the cooling stage Cbb) comprises the same organic solvent which is used as the coolant in stage Ca), when an organic solvent is used in the cooling stage Ca). In an especially preferred variant, at least some of this coolant is fed as a coolant to stage Ca) after it has passed through the at least one cooling stage Cbb). Alternatively, the cooling stage Cbb) may consist of heat exchangers.

Preferably, stage Cb) comprises a plurality of compression stages Cba1) to Cban) and cooling stages Cbb1) to Cbbn), for example four compression stages Cba1) to Cba4) and four cooling stages Cbb1) to Cbb4).

Preferably, step Da) comprises steps Daa) to Dac):

Daa) absorbing the $C_4$ hydrocarbons comprising butadiene and n-butenes in an aromatic hydrocarbon solvent as an absorbent, giving an absorbent stream laden with $C_4$ hydrocarbons and the gas stream d2, Dab) removing oxygen from the absorbent stream laden with $C_4$ hydrocarbons from step Daa) by stripping with an uncondensable gas stream, and Dac) desorbing the $C_4$ hydrocarbons from the laden absorbent stream, giving a $C_4$ product gas stream d1 consisting essentially of $C_4$ hydrocarbons and comprising less than 100 ppm of oxygen.

DETAILED DESCRIPTION OF THE INVENTION

Embodiments of the process of the invention are described in detail below:

The input gas streams a1 used may be pure n-butenes (1-butane and/or cis-2-butene and/or trans-2-butene), but also gas mixtures comprising butenes. Such a gas mixture can be obtained, for example, by nonoxidative dehydrogenation of n-butane. It is also possible to use a fraction which comprises n-butenes as the main constituent and has been obtained from the $C_4$ fraction from naphtha cracking by removal of butadiene and isobutene. In addition, it is also possible to use gas mixtures as input gas stream which comprise pure 1-butene, cis-2-butene, trans-2-butene or mixtures thereof, and which have been obtained by dimerization of ethylene. In addition, the input gas streams used may be gas mixtures which comprise n-butenes and have been obtained by catalytic fluidized bed cracking (fluid catalytic cracking, FCC).

In one embodiment of the process according to the invention, the input gas stream comprising n-butenes is obtained by nonoxidative dehydrogenation of n-butane. Through the coupling of a nonoxidative catalytic dehydrogenation with the oxidative dehydrogenation of the n-butenes formed, it is possible to obtain a high yield of butadiene, based on n-butane used. The nonoxidative catalytic n-butane dehydrogenation gives a gas mixture which, as well as butadiene, comprises 1-butene, 2-butene and unconverted n-butane secondary constituents. Typical secondary constituents are hydrogen, steam, nitrogen, CO and $CO_2$, methane, ethane, ethene, propane and propene. The composition of the gas mixture leaving the first dehydrogenation zone may vary significantly depending on the mode of operation of the dehydrogenation. For instance, in the case of performance of the dehydrogenation while feeding in oxygen and additional hydrogen, the product gas mixture has a comparatively high content of steam and carbon oxides. In the case of modes of operation without feeding of oxygen, the product gas mixture of the nonoxidative dehydrogenation has a comparatively high content of hydrogen.

In step B), the reaction gas mixture comprising the input gas stream a1 comprising n-butenes, an oxygenous gas and an oxygenous cycle gas stream a2, with or without further components, is fed into at least one dehydrogenation zone (the ODH reactor) and the butenes present in the gas mixture are oxidatively dehydrogenated to butadiene in the presence of an oxydehydrogenation catalyst.

Catalysts suitable for the oxydehydrogenation are generally based on an Mo—Bi—O-containing multimetal oxide system which generally additionally comprises iron. In general, the catalyst system also comprises further additional components, for example potassium, cesium, magnesium, zirconium, chromium, nickel, cobalt, cadmium, tin, lead, germanium, lanthanum, manganese, tungsten, phosphorus, cerium aluminum or silicon, iron-containing ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-containing multimetal oxides are Mo—Bi—Fe—Cr—O— or Mo—Bi—Fe—Zr—O— containing multimetal oxides. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$) U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and Mo$_{12}$BiFe$_3$Co$_{4.5}$Ni$_{2.5}$La$_{0.5}$K$_{0.1}$O$_x$), U.S. Pat. No. 3,911,039 (Mo$_{12}$BiFe$_3$Co$_{4.5}$Ni$_{2.5}$Sn$_{0.5}$K$_{0.1}$O$_x$), DE-A 25 30 959 and DE-A 24 47 825 (Mo$_{12}$BiFe$_3$Co$_{4.5}$Ni$_{2.5}$W$_{0.5}$K$_{0.1}$O$_x$).

Suitable multimetal oxides and the preparation thereof are additionally described in U.S. Pat. No. 4,423,281 (Mo$_{12}$BiNi$_8$Pb$_{0.5}$Cr$_3$K$_{0.2}$O$_x$ and Mo$_{12}$Bi$_b$Ni$_7$Al$_3$Cr$_{0.5}$K$_{0.5}$O$_x$), U.S. Pat. No. 4,336,409 (Mo$_{12}$BiNi$_6$Cd$_2$Cr$_3$P$_{0.5}$O$_x$), DE-A 26 00 128 (Mo$_{12}$BiNi$_{0.5}$Cr$_3$P$_{0.5}$Mg$_{7.5}$K$_{0.1}$O$_x$+SiO$_2$) and DE-A 24 40 329 (Mo$_{12}$BiCo$_{4.5}$Ni$_{2.5}$Cr$_3$P$_{0.5}$K$_{0.1}$O$_x$).

Particularly preferred catalytically active multimetal oxides comprising molybdenum and at least one further metal have the general formula (Ia):

$$Mo_{12}Bi_aFe_bCo_cNi_dCr_eX^1_fX^2_gO_y \quad (Ia)$$

where
X$^1$=Si, Mn and/or Al,
X$^2$=Li, Na, K, Cs and/or Rb,
0.2≤a≤1,
0.5≤b≤10,
0≤c≤10,
0≤d≤10,
2≤c+d≤10
0≤e≤2,
0≤f≤10,
0≤g≤0.5,
y=a number which, with the prerequisite of charge neutrality, is determined by the valency and frequency of the elements in (Ia) other than oxygen.

Preference is given to catalysts whose catalytically active oxide composition, of the two metals Co and Ni, has only Co (d=0). Preferred is X$^1$ Si and/or Mn and X$^2$ is preferably K, Na and/or Cs, more preferably X$^2$=K.

The molecular oxygen-comprising gas comprises generally more than 10% by volume, preferably more than 15% by volume and even more preferably more than 20% by volume of molecular oxygen. It is preferably air. The upper limit for the content of molecular oxygen is generally 50% by volume or less, preferably 30% by volume or less and even more preferably 25% by volume or less. In addition, any desired inert gases may be present in the molecular oxygen-comprising gas. Possible inert gases may include nitrogen, argon, neon, helium, CO, CO$_2$ and water. The amount of inert gases, for nitrogen, is generally 90% by volume or less, preferably 85% by volume or less and even more preferably 80% by volume or less. In the case of constituents other than nitrogen, it is generally 10% by volume or less, preferably 1% by volume or less.

For performance of the oxidative dehydrogenation at full conversion of n-butenes, preference is given to a gas mixture having a molar oxygen-butenes ratio of at least 0.5. Preference is given to working at an oxygen:n-butenes ratio of 0.55 to 10. To set this value, the input gas stream can be mixed with oxygen or at least one oxygenous gas, for example air, and optionally additional inert gas or steam. The oxygenous gas mixture obtained is then fed to the oxydehydrogenation.

In addition, it is also possible for inert gases such as nitrogen, and additionally water (in the form of steam), to be present together in the reaction gas mixture. Nitrogen may serve to set the oxygen concentration and to prevent the formation of an explosive gas mixture; the same applies to steam. Steam also serves to control the coking of the catalyst and to remove the heat of reaction.

The reaction temperature in the oxydehydrogenation is generally controlled by a heat exchange medium present around the reaction tubes. Examples of useful liquid heat exchange media of this kind include melts of salts such as potassium nitrate, potassium nitrite, sodium nitrite and/or sodium nitrate, and melts of metals such as sodium mercury and alloys of various metals. It is also possible to use ionic liquids or heat carrier oils. The temperature of the heat exchange medium is between 220 to 490° C. and preferably between 300 to 450° C. and more preferably between 350 and 420° C.

Because of the exothermicity of the reactions which proceed, the temperature in particular sections of the reaction interior during the reaction may be higher than that of the heat exchange medium, and what is called a hotspot develops. The position and magnitude of the hotspot is decided by the reaction conditions, but it can also be regulated through the dilution ratio of the catalyst layer or the flow rate of mixed gas. The difference between hotspot temperature and the temperature of the heat exchange medium is generally between 1-150° C., preferably between 10-100° C. and more preferably between 20-80° C. The temperature at the end of the catalyst bed is generally between 0-100° C., preferably between 0.1-50° C., more preferably between 1-25° C., above the temperature of the heat exchange medium.

The oxydehydrogenation can be performed in all fixed bed reactors known from the prior art, for example in a staged oven, in a fixed bed tubular reactor or shell and tube reactor, or in a plate heat exchanger reactor. A shell and tube reactor is preferred.

Preferably, the oxidative dehydrogenation is performed in fixed bed tubular reactors or fixed bed shell and tube reactors. The reaction tubes (just like the other elements of the shell and tube reactor) are generally manufactured from steel. The wall thickness of the reaction tubes is typically 1 to 3 mm. The internal diameter thereof is generally (uniformly) 10 to 50 mm or 15 to 40 mm, frequently 20 to 30 mm. The number of reaction tubes accommodated in a shell and tube reactor generally runs to at least 1000, or 3000, or 5000, preferably to at least 10 000. Frequently, the number of reaction tubes accommodated in a shell and tube reactor is 15 000 to 30 000, or to 40 000 or to 50 000. The length of the reaction tubes normally extends to a few meters, a typical reaction tube length being in the range from 1 to 8 m, frequently 2 to 7 m, in many cases 2.5 to 6 m.

In addition, the catalyst layer set up in the ODH reactor A may consist of a single layer or of 2 or more layers. These layers may consist of pure catalyst or be diluted with a material which does not react with the input gas stream or components from the product gas of the reaction. In addition, the catalyst layers may consist of unsupported material or supported eggshell catalysts.

The product gas stream leaving the oxidative dehydrogenation comprises, as well as butadiene, generally also unconverted 1-butene and 2-butene, oxygen and steam. As secondary components, it generally further comprises carbon monoxide, carbon dioxide, inert gases (principally nitrogen), low-boiling hydrocarbons such as methane, ethane, ethene, propane and propene, butane and isobutane, with or without hydrogen and with or without oxygen-containing hydrocarbons, called oxygenates. Oxygenates may, for example, be formaldehyde, furan, acetic acid, maleic anhydride, formic acid, methacrolein methacrylic acid, crotonaldehyde, crotonic acid, propionic acid, acrylic acid, methyl vinyl ketone, benzaldehyde, benzoic acid, phthalic anhydride, fluorenone, anthraquinone and butyraldehyde.

The product gas stream at the reactor outlet is characterized by a temperature close to the temperature at the end of the catalyst bed. The product gas stream is then brought to a temperature of 150 to 400° C., preferably 160 to 300° C., more preferably 170 to 250° C. It is possible to insulate the line through which the product gas stream flows, or to use a heat exchanger, in order to keep the temperature within the desired range. Any heat exchanger system is possible, provided that this system can be used to keep the temperature of the product gas at the desired level. Examples of a heat exchanger include spiral heat exchangers, plate heat exchangers, double tube heat exchangers, multitubes heat exchangers, boiler-spiral heat exchangers, boiler-shell heat exchangers, liquid-liquid contact heat exchangers, air heat exchangers, direct contact heat exchangers and fin tube heat exchangers. Since, while the temperature of the product gas is set to the desired temperature, some of the high-boiling by-products present in the product gas can precipitate out, the heat exchanger system should therefore preferably have two or more heat exchangers. If two or more heat exchangers provided are arranged in parallel in this case, and distributed cooling of the product gas obtained in the heat exchangers is thus enabled, the amount of high-boiling by-products which are deposited in the heat exchangers decreases, and hence the service life thereof can be extended. As an alternative to the abovementioned method, the two or more heat exchangers provided may be arranged in parallel. The product gas is supplied to one or more, but not to all, heat exchangers, which are succeeded by other heat exchangers after a certain operation period. In the case of this method, the cooling can be continued, some of the heat of reaction can be recovered and, in parallel, the high-boiling by-products deposited in one of the heat exchangers can be removed. It is possible to use e a solvent as an above mentioned organic solvent, provided that it is capable of dissolving the high-boiling by-products. Examples are aromatic hydrocarbon solvents, for example toluene and xylenes, and alkaline aqueous solvent, for example the aqueous solution of sodium hydroxide.

Subsequently, a majority of the high-boiling secondary components and of the water is removed from the product gas stream by cooling and compression. This stage is also referred to hereinafter as the quench. This quench may consist of only one stage or of several stages. The cooling can be effected by contacting with a coolant, preferably an organic solvent. The cooling media used are organic solvents, preferably aromatic hydrocarbons, more preferably toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is also given to aromatic hydrocarbons having a boiling point at 1013.25 hPa of more than 120° C., or mixtures thereof.

Preference is given to a two-stage quench, meaning that stage Ca comprises two cooling stages Ca1) and Ca2), in which the product gas stream b is contacted with the organic solvent.

In general, the product gas, according to the presence and temperature level of any heat exchanger upstream of the quench, has a temperature of 100-440° C. The product gas is contacted with the cooling medium in the 1st quench stage. In this case, the cooling medium can be introduced through a nozzle, in order to achieve very efficient mixing with the product gas. For the same purpose, it is possible to introduce internals, for example further nozzles, in the quench stage, through which the product gas and the cooling medium pass together. The coolant inlet into the quench is designed such that blockage by deposits in the region of the coolant inlet is minimized.

In general, the product gas is cooled in the first quench stage to 5-180° C., preferably to 30-130° C. and even more preferably to 60-110° C. The temperature of the coolant medium at the inlet may generally be 25-200° C., preferably 40-120° C., especially preferably 50-90° C. The pressure in the first quench stage is not particularly restricted, but is generally 0.01-4 bar (g), preferably 0.1-2 bar (g) and more preferably 0.2-1 bar (g). If any great amounts of high-boiling by-products are present in the product gas, high-boiling by-products may readily polymerize and result in deposits of solids which are caused by high-boiling by-products in this process section. In general, the quench stage is configured as a cooling tower. The cooling medium used in the cooling tower is frequently used in circulating form. The circulation flow rate of the cooling medium in liters per hour, based on the mass flow rate of butadiene in grams per hour, may generally be 0.0001-5 l/g, preferably 0.001-1 l/g and more preferably 0.002-0.2 l/g.

The temperature of the cooling medium in the pot may generally be 27-210° C., preferably 45-130° C., especially preferably 55-95° C. Since the loading of the cooling medium with secondary components increases over the course of time, a portion of the laden cooling medium can be drawn off from the circulation as a purge stream, and the circulation volume can be kept constant by adding unladen cooling medium. The ratio of output volume and addition volume depends on the steam loading of the product gas and the product gas temperature at the end of the first quench stage.

According to the temperature, pressure and water content of the product gas, there may be condensation of water in the first quench stage. In this case, an additional aqueous phase may form, which may additionally comprise water-soluble secondary components. This can then be drawn off in the bottom of the quench stage. Preference is given to operation in which no aqueous phase forms in the first quench stage.

The cooled product gas stream, which may have been freed of secondary components, can then be sent to a second quench stage. In this stage, it can be contacted again with a cooling medium.

The choice of coolant is not particularly restricted. The cooling media used are preferably organic solvents, more preferably aromatic hydrocarbons, in particular toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is also given to aromatic hydrocarbons having a boiling point at 1013.25 hPa of more then 120° C., or mixtures thereof.

In general, the product gas, up to the gas outlet of the second quench stage, is cooled to 5 to 100° C., preferably to 15 to 85° C. and even more preferably to 30 to 70° C. The coolant can be fed in in countercurrent to the product gas. In this case, the temperature of the coolant medium at the coolant outlet may be 5 to 100° C., preferably 15 to 85° C., especially preferably 30 to 70° C. The pressure in the second quench stage is not particularly restricted, but is generally 0.01 to 4 bar (g), preferably 0.1 to 2 bar (g) and more preferably 0.2 to 1 bar (g). The second quench stage is preferably configured as a cooling tower. The cooling medium used in the cooling tower is frequently used in circulating form. The circulation flow rate of the cooling medium in liters per hour, based on the mass flow rate of butadiene in grams per hour, may generally be 0.0001 to 5 l/g, preferably 0.3001 to 1 l/g and more preferably 0.002 to 0.2 l/g.

According to the temperature, pressure and water content of the product gas, there may be condensation of water in the second quench stage. In this case, an additional aqueous phase may form, which may additionally comprise water-soluble secondary components. This can then be drawn off in the bottom of the quench stage. The temperature of the cooling medium in the pot may generally be 20 to 210° C., preferably 35 to 120° C., especially preferably 45 to 85° C. Since the loading of the cooling medium with secondary components increases over the course of time, a portion of the laden cooling medium can be drawn off from the circulation as a purge stream, and the circulation volume can be kept constant by adding unladen cooling medium.

In order to achieve very good contact of product gas and cooling medium, internals may be present in the second quench stage. Internals of this kind include, for example, bubble-cap, centrifugal and/or sieve trays, columns having structured packings, for example sheet metal packings having a specific surface area of 100 to 1000 m$^2$/m$^3$, such as Mellapak® 250 Y, and columns having random packings.

The coolant circulation streams of the two quench stages may either be separate from one another or combined with one another. For example, the stream may be fed into the stream or replace it. The desired temperature of the circulation streams can be set by means of suitable heat exchangers.

In a preferred embodiment of the invention, the cooling stage Ca) is thus performed in two stages, in which case the coolant laden with secondary components from the second stage Ca2) is conducted into the first stage Ca1). The coolant withdrawn from the second stage Ca2) comprises a lower level of secondary components than the coolant withdrawn from the first stage Ca1).

In order to minimize the entrainment of liquid constituents from the quench into the offgas line, suitable construction measures, for example the installation of a demister, can be taken. In addition, high-boiling substances which are not separated from the product gas in the quench can be removed from the product gas through further construction measures, for example further gas scrubbing operations.

A gas stream is obtained, in which comprises n butane, 1-butene, 2-butenes and butadiene, with or without oxygen hydrogen and steam, and small amounts of methane, ethane, ethene, propane and propene, isobutane, carbon oxides, inert gases and portions of the coolant used in the quench. In addition, traces of high-boiling components which have not been removed quantitatively in the quench may remain in this gas stream. Such high-boiling components include, for example, methyl vinyl ketone, methyl ethyl ketone crotonaldehyde, acrylic acid, propionic acid, maleic anhydride, ethylbenzene, styrene, furanone, benzoic acid, benzaldehyde, fluorenone and anthraquinone. In addition, this gas stream may comprise formaldehyde, methacrolein and/or furan.

Subsequently, the gas stream b' from the cooling step Ca), which has been depleted of high-boiling secondary components, is cooled in step Cb) in at least one compression stage Cba) and preferably in at least one cooling stage Cbb).

The product gas stream from the quench is compressed in at least one compression stage and subsequently cooled further in the cooling apparatus, forming at least one condensate stream comprising water. If a coolant other than water is used in the quench, it is also possible for the coolant used in the quench to condense out, and it may form a separate phase. What remains is a gas stream comprising butadiene, 1-butene, 2-butenes, oxygen and steam, with or without low-boiling hydrocarbons such as methane, ethane, ethene, propane and propene, butane and isobutane, with or without carbon oxides and with or without inert gases. In addition, this product gas stream may also comprise traces of high-boiling components.

The compression and cooling of the gas stream can be effected in one or more stages (n stages). In general, compression is effected overall from a pressure in the range from 1.0 to 4.0 bar (absolute) to a pressure in the range from 3.5 to 20 bar (absolute). Each compression stage is followed by a cooling stage in which the gas stream is cooled to a temperature in the range from 15 to 60° C. The cooling is preferably effected by contacting with an organic solvent as a coolant. Alternatively, it is also possible to use heat exchangers. In the case of multistage compression, the condensate stream may thus also comprise a plurality of streams. The condensate stream consists in major portions of water (aqueous phase) and any coolant used in the quench (organic phase). Both streams (aqueous and organic phase) may additionally comprise, to a minor extent, secondary components such as low boilers, $C_4$ hydrocarbons, oxygenates and carbon oxides.

In order to cool the stream and/or to remove further secondary components from the stream, the condensed quench coolant can be cooled in a heat exchanger and recycled into the apparatus as coolant. Since the loading of this cooling medium with secondary components increases over the course of time, a portion of the laden cooling medium can be drawn off from the circulation, and the circulation volume of the cooling medium can be kept constant by adding unladen coolant.

The coolant, which is added as a cooling medium, this likewise preferably consists of the aromatic hydrocarbon solvent used as the quench coolant.

The condensate stream can be recycled into the circulation stream of the quench. As a result, the $C_4$ components absorbed in the condensate stream can be brought back into the gas stream, and hence the yield can be increased. Suitable compressors are, for example, turbo compressors, rotary piston compressors and reciprocating piston compressors. The compressors may be driven, for example, with an electric motor, an expander or a gas or steam turbine. Typical compression ratios (inlet pressure:outlet pressure) per compressor stage are between 1.5 and 3.0 according to the design. The compressed gas is cooled with organic solvent-purged heat exchangers or organic quench stages, which may take the form, for example, of shell and tube, spiral or plate heat exchangers. The coolants used in the heat exchangers are cooling water or heat carrier oils. In addition, preference is given to using air cooling with use of blowers.

The gas stream c2 comprising butadiene, n-butenes, oxygen, low-boiling hydrocarbons (methane, ethane, ethene, propane, propene, n-butane, isobutane), with or without steam, with or without carbon oxides and with or without inert gases and with or without traces of secondary components is fed as an output stream to further processing.

In a step Da), uncondensable and low-boiling gas constituents comprising oxygen, low-boiling hydrocarbons (methane, ethane, ethene, propane, propene), carbon oxides and inert gases are separated in an absorption column from the process gas stream c2 by absorption of the $C_4$ hydrocarbons in an aromatic hydrocarbon solvent as a high-boiling absorbent and subsequent desorption of the $C_4$ hydrocarbons. Preferably, step Da) comprises steps Daa) to Dac):

Daa) absorbing the $C_4$ hydrocarbons comprising butadiene and n-butenes in an aromatic hydrocarbon solvent as an absorbent, giving an absorbent stream laden with $C_4$ hydrocarbons and the gas stream d2, Dab) removing oxygen from the absorbent stream laden with $C_4$ hydrocarbons from step Daa) by stripping with an uncondensable gas stream, and Dac) desorbing the $C_4$ hydrocarbons from the laden absorbent stream, giving a $C_4$ product gas stream d1 consisting essentially of $C_4$ hydrocarbons.

For this purpose, in the absorption stage, the gas stream c2 is contacted with the absorbent and the $C_4$ hydrocarbons are absorbed in the absorbent, giving an absorbent laden with $C_4$ hydrocarbons and a gas stream d2 comprising the other gas constituents, and the latter is at least partly recycled as cycle gas stream into the oxidative dehydrogenation. In a desorption stage, the $C_4$ hydrocarbons are released again from the absorbent.

The absorbents used are organic solvents, preferably aromatic hydrocarbons, more preferably toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is also given to aromatic hydrocarbons having a boiling point at 1013.25 hPa of more than 120° C., or mixtures thereof. More particularly, in the removal stage Da), the same aromatic hydrocarbon solvent is used as in the preceding cooling stage Ca), when an organic solvent is used in the cooling stage Ca). Preferred absorbents are solvents having a dissolution capacity for organic peroxides of at least 1000 ppm (mg of active oxygen/kg of solvent) in a preferred embodiment, the absorbent used for the absorption is mesitylene.

The absorption stage can be conducted in any desired suitable absorption column known to those skilled in the art. The absorption can be effected by simply passing the product gas stream through the absorbent. However, it can also be effected in columns or in rotary absorbers. It is possible to work in concurrent, countercurrent or crosscurrent. The absorption is preferably conducted in countercurrent. Suitable absorption columns are, for example, tray columns having bubble-cap, centrifugal and/or sieve trays, columns having structured packings, for example sheet metal packings having a specific surface area of 100 to 1000 $m^2/m^3$, such as Mellapak® 250 Y, and columns having random packings. Also useful, however, are trickle towers and spray towers, graphite block absorbers, surface absorbers such as thick-layer and thin-layer absorbers, and also rotary columns, pan scrubbers, cross-spray scrubbers and rotary scrubbers.

In one embodiment, the gas stream c2 comprising butadiene, n-butenes and the low-boiling and uncondensable gas constituents is supplied to an absorption column in the lower region. In the upper region of the absorption column, the absorbent is applied.

At the top of the absorption column, a gas stream d2 is drawn off, comprising essentially oxygen, low-boiling hydrocarbons (methane, ethane, ethene, propane, propene) and the aromatic hydrocarbon solvent, with or without $C_4$ hydrocarbons (butane, butenes, butadiene), with or without inert gases, with or without carbon oxides and with or without steam. This stream is at least partly sent to the ODH reactor as cycle gas stream a2. It is thus possible, for example, to adjust the inlet stream of the ODH reactor to the desired $C_4$ hydrocarbon content. In general, optionally after removal of a purge gas stream, at least 30% by volume, preferably at least 50% by volume, of the gas stream d2 is recycled as cycle gas stream a2 into the oxidative dehydrogenation zone.

In general, the recycle stream is 10 to 70% by volume, preferably 30 to 60% by volume, based on the sum total of all the streams fed into the oxidative dehydrogenation B).

The purge gas stream can be subjected to a thermal or catalytic post combustion. More particularly, it can be utilized thermally in a power plant.

At the bottom of the absorption column, in a further column, purging with a gas results in discharge of residues of oxygen dissolved in the absorbent. The remaining oxygen content is preferably sufficiently small that the stream d1 which comprises butane, butene and butadiene leaving the desorption column comprises only a maximum of 100 ppm of oxygen.

The stripping of the oxygen in step Dab) can be performed in any desired suitable column known to those skilled in the art. The stripping can be effected by simply passing uncondensable gases, preferably inert gases such as nitrogen, through the laden absorption solution. C4 additionally stripped out is washed back into the absorption solution in the upper portion of the absorption column, by passing the gas stream back into this absorption column. This can be effected either by means of pipe connection of the stripper column or direct mounting of the stripper column below the absorber column. This direct coupling, can be effected since the pressure in the stripping column section and absorption column section is the same in accordance with the invention. Suitable stripping columns are, for example, tray columns having bubble-cap, centrifugal and/or sieve trays, columns having structured packings, for example sheet metal packings having a specific surface area of 100 to 1000 $m^2/m^3$, such as Mellapak® 250 Y, and columns having random packings. Also useful, however, are trickle towers and spray towers, and also rotary columns, pan scrubbers, cross-spray scrubbers and rotary scrubbers. Suitable gases are, for example, nitrogen or methane.

The absorbent stream laden with $C_4$ hydrocarbons may include water. This can be separated from the absorbent as a stream in a decanter, such that a stream comprising only the water dissolved in the absorbent is obtained.

The absorbent stream d2 laden with $C_4$ hydrocarbons, which has been very substantially freed of the water, can be heated in a heat exchanger and then passed into a desorption column. In one process variant, the desorption step Dc) is performed by decompressing and/or heating the laden absorbent. The preferred process variant is the utilization of a reboiler in the bottom of the desorption column.

The absorbent regenerated in the desorption stage can be cooled in a heat exchanger and recycled into the absorption stage. Low boilers present in the process gas stream, for example ethane or propane, and high-boiling components such as benzaldehyde, maleic anhydride and phthalic anhydride, can accumulate in the circuiting stream. In order to limit the accumulation, a purge stream can be drawn off. This can be separated in a distillation column according to the prior art into low boilers, regenerated absorbent and high boilers.

The $C_4$ product gas stream d1 consisting essentially of n-butane, n-butenes and butadiene comprises generally 20 to 80% by volume of butadiene, 0 to 80% by volume of n-butane, 0 to 10% by volume of 1-butene and 0 to 50% by volume of 2-butenes, where the total amount is 100% by volume. In addition, small amounts of isobutane nay be present.

A portion of the condensed top discharge from the desorption column comprising principally C4 hydrocarbons is recycled into the top of the column, in order to increase the separation performance of the column.

The liquid or gaseous $C_4$ product streams leaving the condenser can subsequently be separated by extractive distillation in step E) with a butadiene-selective solvent into a stream comprising butadiene and the selective solvent, and a stream comprising n-butenes.

The extractive distillation can be performed, for example, as described in "Erdöl und Kohle-Erdgas-Petrochemie", volume 34 (8), pages 343 to 346, or "Ullmanns Enzyklopädie der Technischen Chemie", volume 9, 4th edition 1975, pages 1 to 18. For this purpose, the $C_4$ product gas stream is contacted with an extractant, preferably an N-methylpyrrolidone (NMP)/water mixture, in an extraction zone. The extraction zone generally takes the form of a scrubbing column comprising trays, random packings or structured packings as internals. This generally has 30 to 70 theoretical plates, in order that a sufficiently good separating action is achieved. Preferably, the scrubbing column has a re-scrubbing zone in the top of the column. This re-scrubbing zone serves for recovery of the extractant present in the gas phase with the aid of a liquid hydrocarbon return stream, for which the top fraction is condensed beforehand. The mass ratio of extractant to $C_4$ product gas stream in the feed to the extraction zone is generally 10:1 to 20:1. The extractive distillation is preferably operated at a bottom temperature in the range from 100 to 250° C., especially at a temperature in the range from 110 to 210° C., a top temperature in the range from 10 to 100° C., especially in the range from 20 to 70° C., and a pressure in the range from 1 to 15 bar, especially in the range from 3 to 8 bar. The extractive distillation column has preferably 5 to 70 theoretical plates.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, especially N-methylpyrrolidone (NMP). In general, alkyl-substituted lower aliphatic acid amides or N-alkyl-substituted cyclic acid amides are used. Particularly advantageous are dimethylformamide, acetonitrile, furfural and especially NMP.

However, it is also possible to use mixtures of these extractants with one another, for example of NMP and acetonitrile, mixtures of these extractants with co-solvents and/or tert-butyl ethers, e.g. methyl tert-butyl ether, ethyl tert-butyl ether, propyl tea-butyl ether, n- or isobutyl tert-butyl ether. NMP is particularly suitable, preferably in aqueous solution, preferably with 0 to 20% by weight of water, more preferably with 7 to 10% by weight of water, especially with 8.3% by weight of water.

The top product stream from the extractive distillation column comprises essentially butane and butenes and small amounts of butadiene and is drawn off in gaseous or liquid form. In general, the stream consisting essentially of n-butane and 2-butene comprises up to 100% by volume of n-butane, 0 to 50% by volume of 2-butene, and 0 to 3% by volume of further constituents such as isobutane, isobutene, propane, propene and $C_5^+$ hydrocarbons.

The stream consisting essentially of n-butane and 2-butenes can be fed fully or partly into the $C_4$ feed of the ODH reactor. Since the butene isomers in this recycle stream consist essentially of 2-butenes, and 2-butenes are generally oxidatively dehydrogenated more slowly to butadiene than 1-butene, this recycle stream can be catalytically isomerized before being fed into the ODH reactor. As a result, it is possible to adjust the isomer distribution in accordance with the isomer distribution present at thermodynamic equilibrium.

In a step F), the stream comprising butadiene and the selective solvent is distillatively separated into a stream consisting essentially of the selective solvent and a stream comprising butadiene.

The stream obtained at the bottom of the extractive distillation column generally comprises the extractant, water, butadiene and small proportions of butenes and butane and is fed to a distillation column. Butadiene can be obtained therein overhead or as a side draw. At the bottom of the distillation column, a stream comprising extractant, with or without water, is obtained, the composition of the stream comprising extractant and water corresponding to the composition as added to the extraction. The stream comprising extractant and water is preferably passed back into the extractive distillation.

If the butadiene is obtained via a side draw, the extraction solution thus drawn off is transferred into a desorption zone, and the butadiene is once again desorbed and re-scrubbed out of the extraction solution. The desorption zone may be configured, for example, in the form of a scrubbing column having 2 to 30 and preferably 5 to 20 theoretical plates, and optionally a re-scrubbing zone having, for example, 4 theoretical plates. This re-scrubbing zone serves for recovery of the extractant present in the gas phase with the aid of a liquid hydrocarbon return stream, for which the top fraction is condensed beforehand. As internals, structured packings, trays or random packings are provided. The distillation is preferably performed at a bottom temperature in the range from 100 to 300° C., especially in the range from 150 to 200° C., and a top temperature in the range from 0 to 70° C., especially in the range from 10 to 50° C. The pressure in the distillation column is preferably in the range from 1 to 10 bar. In general, a reduced pressure and/or an elevated temperature exists in the desorption zone compared to the extraction zone.

The product of value stream obtained at the top of the column comprises generally 90 to 100% by volume of butadiene, 0 to 10% by volume of 2-butene and 0 to 10% by volume of n-butane and isobutane. For further purification of the butadiene, a further distillation can be performed in accordance with the prior art.

EXAMPLES

Catalyst Preparation
2 solutions A and B were prepared.
Solution A:
A 10 l stainless steel pot was initially charged with 3200 g of water, and 5.2 g of a KOH solution (32% by weight of KOH) were added while stirring by means of an anchor stirrer. The solution was heated to 60° C. Then 1066 g of an ammonium heptamolybdate solution $((NH_4)_6Mo_7O_{24} \cdot 4 H_2O$, 54% by weight of Mo) were added in portions over a period of 10 minutes. The resulting suspension was stirred for a further 10 minutes.
Solution B:
A 5 l stainless steel pot was initially charged with 1771 g of a cobalt(II) nitrate solution (12.3% by weight of Co) and heated to 60° C. while stirring (anchor stirrer). Then 645 g of an iron(III) nitrate solution (13.7% by weight of Fe) were added in portions over a period of 10 minutes while maintaining the temperature. The resulting solution was stirred for a further 10 min. Then 619 g of a bismuth nitrate solution (10.7% by weight of Bi) were added while maintaining the temperature. After stirring for a further 10 minutes, 109 g of chromium(III) nitrate in solid form were added in portions and the resulting dark red solution was stirred for a further 10 min.

While maintaining the 60° C. solution B was added to solution A by means of a peristaltic pump within 15 min. During the addition and thereafter, the mixture was stirred by means of an intensive mixer (Ultra-Turrax). On completion of addition, the mixture was stirred for another 5 minutes.

The resulting suspension was spray-dried in a spray tower from NIRO (spray head No. FOA1, speed 25 000 rpm) over a period of 1.5 h. For this period, the reservoir temperature was kept at 60° C. The gas input temperature of the spray tower was 300° C., the gas output temperature 110° C. The resulting powder had a particle size (d50) of less than 40 μm.

The resulting powder was mixed with 1% by weight of graphite, compacted twice with pressure 9 bar and comminuted through a screen with mesh size 0.8 mm. The spell was, in turn, mixed with 2% by weight of graphite and the mixture was pressed with a Kilian S100 tableting press into 5×3×2 mm rings (external diameter×length×internal diameter).

The resulting catalyst precursor was calcined batchwise (500 g) in an air circulation oven from Heraeus, Germany (model K, 750/2 S, capacity 55 l). The following program was used for this purpose:
heat to 130° C. within 72 minutes, hold for 72 minutes
heat to 190° C. within 36 minutes, hold for 72 minutes
heat to 220° C. within 36 minutes, hold for 72 minutes
heat to 265° C. within 36 minutes, hold for 72 minutes
heat to 380° C. within 93 minutes, hold for 187 minutes
heat to 430° C. within 93 minutes, hold for 187 minutes
heat to 490° C. within 93 minutes, hold for 467 minutes.

After the calcination, the catalyst of the calculated stoichiometry $Mo_{12}Co_7Fe_3Bi_{0.6}K0.0_8Cr0.5Ox$ was obtained.

The calcined rings were ground to a powder. This precursor composition was used to coat three batches of support bodies (steatite rings having dimensions 5×3×2 mm (external diameter×height×internal diameter). To this end, 1054 g each time of the support were initially charged in a coating drum (diameter 255 cm, angle of inclination of the central drum axis relative to the horizontal=30°). The drum was set in rotation (36 rpm). An atomizer nozzle operated with compressed air was used to spray about 60 ml of liquid binder (1:3 glycerol:water mixture) onto the support over the course of about 25 min (spraying air 200 l (STP)/h). The nozzle was installed such that the spray cone wetted the support bodies conveyed within the drum in the upper half of the roll-off zone. A total of 191 g of the fine pulverulent precursor composition of the ground catalyst were introduced into the drum by means of a powder screw, with the point of powder addition within the roll-off zone, but below the spray cone. The powder addition was metered in in such a way as to give rise to homogeneous distribution of the powder on the surface. On completion of the coating, the resulting eggshell catalyst composed of precursor composition and the support body was dried in a drying cabinet at 300° C. for 4 hours. The active composition content was 15% by weight.

Dehydrogenation Experiments

Dehydrogenation experiments were conducted in a screening reactor. The screening reactor was a salt bath reactor having a length of 125 cm and an internal diameter of 14.9 mm, and a thermowell having an external diameter of 3.17 mm. In the thermowell was a multiple thermocouple having 7 measurement points. The lower 4 measurement points were at a distance of 10 cm, and the upper 4 measurement points at a distance of 5 cm. The butanes/butenes mixture was metered in in liquid form through a coriolis flowmeter at about 10 bar, mixed in a static mixer and then decompressed and vaporized in a heated vaporizer zone. This gas was then mixed with nitrogen and passed with a steatite bed in a preheater. Water was metered in in liquid form and vaporized in an air stream in a vaporizer coil. The air/steam mixture was combined with the $N_2$/raffinate II/butane mixture in the lower region of the preheater. The completely mixed reactant gas was then supplied to the reactor, and an analysis stream for the online GO measurement can be drawn off. An analysis stream, which can be analyzed by online GC measurement, is likewise drawn off from the product gas leaving the reactor. A pressure-regulating valve follows downstream of the branch in the analysis line, which keeps the pressure level at 1 bar gauge upstream of the reactor.

Atop the catalyst base at the lower end of the screening reactor, a downstream bed of length 9.5 cm, consisting of 24 g of steatite spheres having a diameter of 3.5-4.5 mm, was introduced. Thereafter, 120 g of the eggshell catalyst were introduced into the reactor (bed volume 108 mm, bed height 65 cm). The catalyst bed was followed by an upstream bed of length 6 cm, consisting of 16 g of steatite spheres having a diameter of 3.5-4.5 mm.

TABLE 1

Composition of the C4-containing gas

| i-Butane | n-Butane | t-2-Butene | c-2-Butene | 1-Butene | i-Butene |
|---|---|---|---|---|---|
| 4.0 mol % | 20.5 mol % | 39.5 mol % | 16.0 mol % | 16.5 mol % | 3.5 mol % |

The catalyst was activated at 400° C. over the course of 24 h with a mixture of 10% by volume of oxygen, 80% by volume of nitrogen and 10% by volume of steam (total volume flow rate 150 l (STP)/h). Thereafter, the reactor was fed with 150 l (STP)/h of a reaction gas (10.4% by volume of C4-containing gas, for composition see table 1; 12.2% by volume of $O_2$; 10.3% by volume of steam; remainder $N_2$) at a salt bath temperature of 380° C. for 6 days. Within this period, the constituents of the reactant and product gases were analyzed by means of online GC. The conversion (X) and selectivity (S) parameters calculated in the examples were determined as follows:

$$X = \frac{\text{mol(butenes}_{in}) - \text{mol(butenes}_{out})}{\text{mol(butenes}_{in})}$$

$$S = \frac{\text{mol(butadiene}_{out}) - \text{mol(butadiene}_{in})}{\text{mol(butenes}_{in}) - \text{mol(butenes}_{out})}$$

where mol(XXXin) is the molar amount of component XXX at the reactor inlet, mol(XXXout) is the molar amount of component XXX at the reactor outlet, and butenes is the sum total of 1-butene, cis-2-butene, trans-2-butene and isobutene.

Example 1

The reactor was operated with the reactant gas composition specified in table 2 and under the above mentioned reaction conditions for 24 hours. Within this period, at a butenes conversion of 87.2%, a selectivity for butadiene of 84% was found.

Example 2

Thereafter, the reactor was operated with the feed composition specified in table 2 and under the above mentioned reaction conditions for a further 24 hours. In addition, 0.34% by volume of mesitylene was added to the reactant gas within this time. Within this period, the butenes conversion fell to 63.4% at a selectivity for butadiene of 87.1%.

Example 3

Thereafter, the reactor was operated with the feed composition specified in table 2 and under the above mentioned reaction conditions for a further 24 hours. In addition, 0.43% by volume of mesitylene was added to the reactant gas within this time. Within this period, the butenes conversion fell to 57.1% at a selectivity for butadiene of 85.8%.

Example 4

Thereafter, the reactor was operated with the feed composition specified in table 2 and under the above mentioned reaction conditions for a further 24 hours. In addition, 0.21% by volume of mesitylene was added to the reactant gas within this time. Within this period, the butenes conversion rose to 71.4% at a selectivity for butadiene of 86.9%.

Example 5

Thereafter, the reactor was operated with the feed composition specified in table 2 under the above mentioned reaction conditions for a further 24 hours. In this time, no mesitylene was added to the reactant gas. Within this period, the butenes conversion rose to 85.6% at a selectivity for butadiene of 87.6%.

TABLE 2

Reactant gas composition, butenes conversion and butadiene selectivity

| Example | C4 gas [% by vol.] | O2 [% by vol.] | N2 [% by vol.] | H2O [% by vol.] | Mesitylene [% by vol.] | Conversion of butenes [%] | Selectivity for butadiene [%] |
|---|---|---|---|---|---|---|---|
| 1 | 10.4 | 11.9 | remainder | 10.2 | — | 87.2 | 84.0 |
| 2 | 10.2 | 11.9 | remainder | 10.3 | 0.34 | 63.4 | 87.1 |
| 3 | 10.6 | 12.0 | remainder | 10.2 | 0.43 | 57.1 | 85.8 |
| 4 | 10.3 | 12.0 | remainder | 10.1 | 0.21 | 71.4 | 86.9 |
| 5 | 10.1 | 12.3 | remainder | 10.4 | — | 85.6 | 87.6 |

The invention claimed is:

1. A process for preparing butadiene from n-butenes, comprising the steps of:
   A) providing an input gas stream a1 comprising n-butenes;
   B) feeding the input gas stream a1 comprising n-butenes, an oxygenous gas and an oxygenous cycle gas stream a2 into at least one oxidative dehydrogenation zone and oxidatively dehydrogenating n-butenes to butadiene, giving a product gas stream b comprising butadiene, unconverted n-butenes, steam, oxygen, low-boiling hydrocarbons and high-boiling secondary components, with or without carbon oxides and with or without inert gases;
   Ca) cooling the product gas stream b and optionally at least partly removing high-boiling secondary components and steam, giving a product gas stream b';
   Cb) compressing and cooling the product gas stream b in at least one compression and cooling stage, giving at least one aqueous condensate stream c1 and one gas stream c2 comprising butadiene, n-butenes, steam, oxygen and low-boiling hydrocarbons, with or without carbon oxides and with or without inert gases;
   Da) absorbing the C4 hydrocarbons comprising butadiene and n-butenes in an aromatic hydrocarbon solvent as an absorbent and removing uncondensable and low-boiling gas constituents comprising oxygen, low-boiling hydrocarbons, any carbon oxides, aromatic hydrocarbon solvent and any inert gases as gas stream d2 from the gas stream c2, giving an absorbent stream laden with C4 hydrocarbons and the gas stream d2, and then desorbing the C4 hydrocarbons from the laden absorbent stream, giving a C4 product gas stream d1; and
   Db) at least partly recycling the gas stream d2 as the oxygenous cycle gas stream a2 into the oxidative dehydrogenation zone,
   wherein a content of aromatic hydrocarbon solvent in the oxygenous cycle gas stream a2 is limited to less than 0.2% by volume by
   (a) contacting the gas stream d2 which leaves the removal stage Da) with a liquid absorbent for the aromatic hydrocarbon solvent in a further column,
   (b) contacting the gas stream d2 which leaves the removal stage Da) with a solid adsorbent which adsorbs the aromatic hydrocarbon solvent,
   (c) contacting the gas stream d2 which leaves the removal stage Da) with a heat exchanger in the form of a condenser, with at least partial deposition of the aromatic hydrocarbon solvent present in stream d2 as a liquid phase through cooling,
   (d) conducting a thermal or catalytic post combustion of the aromatic hydrocarbon solvent, or
   (e) providing, in the absorption column used in step Da), an apparatus which reduces the entrainment of liquid constituents from the absorption column into the gas stream d2.

2. The process according to claim 1, wherein the aromatic hydrocarbon solvent used as the absorbent in step Da) is selected from the group consisting of toluene, o-, m-, p-xylene, mesitylene, monoethylbenzene, diethylbenzene, triethylbenzene, monoisopropylbenzene, diisopropylbenzene, triisopropylbenzene and mixtures thereof.

3. The process according to claim 2, wherein the aromatic hydrocarbon solvent is mesitylene.

4. The process according to claim 1, wherein the proportion of the cycle gas stream a2 is 10 to 70% by volume, based on the sum total of all the gas streams fed into the oxidative dehydrogenation zone.

5. The process according to claim 1, which further comprises the following additional steps of:
E) separating the $C_4$ product stream d1 by extractive distillation with a butadiene-selective solvent into a stream e1 comprising butadiene and the selective sovent and a stream e2 comprising n-butenes:
F) distilling the stream e2 comprising butadiene and the selective solvent to give a stream f1 comprising the selective solvent and a stream f2 comprising butadiene.

6. The process according to claim 1, wherein step Da) comprises steps Daa) to Dac):
Daa) absorbing the $C_4$ hydrocarbons comprising butadiene and n-butenes in the aromatic hydrocarbon solvent as an absorbent, giving an absorbent stream laden with $C_4$ hydrocarbons and the gas stream d2,
Dab) removing oxygen from the absorbent stream laden with $C_4$ hydrocarbons from step Daa) by stripping with an uncondensable gas stream, and
Dac) desorbing the $C_4$ hydrocarbons from t be laden absorbent stream, giving a $C_4$ product gas stream d1 consisting essentially of $C_4$ hyrocarbons.

* * * * *